United States Patent
Wahr et al.

(10) Patent No.: US 11,771,492 B2
(45) Date of Patent: Oct. 3, 2023

(54) SYSTEMS AND METHODS FOR IMPROVED DELIVERY OF EXPANDABLE CATHETER ASSEMBLIES INTO BODY LUMENS

(71) Applicant: Nuvaira, Inc., Plymouth, MN (US)

(72) Inventors: Dennis Wahr, Minneapolis, MN (US); Larry Wales, Maplewood, MN (US); Steven P. Mertens, Plymouth, MN (US)

(73) Assignee: Nuvaira, Inc., Plymouth, MN (US)

( * ) Notice: Subject to any disclaimer, the term of this patent is extended or adjusted under 35 U.S.C. 154(b) by 501 days.

(21) Appl. No.: 16/308,757

(22) PCT Filed: Jun. 9, 2017

(86) PCT No.: PCT/US2017/036773
§ 371 (c)(1),
(2) Date: Dec. 10, 2018

(87) PCT Pub. No.: WO2017/214516
PCT Pub. Date: Dec. 14, 2017

(65) Prior Publication Data
US 2019/0142511 A1  May 16, 2019

Related U.S. Application Data

(60) Provisional application No. 62/347,980, filed on Jun. 9, 2016.

(51) Int. Cl.
*A61B 18/14* (2006.01)
*A61B 18/12* (2006.01)
*A61B 18/00* (2006.01)

(52) U.S. Cl.
CPC .......... *A61B 18/1492* (2013.01); *A61B 18/00* (2013.01); *A61B 18/12* (2013.01);
(Continued)

(58) Field of Classification Search
CPC ..... A61B 18/1492; A61B 18/12; A61B 18/00; A61B 18/14; A61B 2018/00023;
(Continued)

(56) References Cited

U.S. PATENT DOCUMENTS 5,759,187 A   6/1998   Nakao et al.
5,893,868 A * 4/1999   Hanson ................. A61F 2/0095
                                                    606/198

(Continued)

FOREIGN PATENT DOCUMENTS

CN    103889348 A    6/2014
JP    2014530644 A   11/2014
(Continued)

OTHER PUBLICATIONS

PCT International Search Report for PCT/US2017/036773, dated Sep. 12, 2017, 3 pages.
(Continued)

*Primary Examiner* — Linda C Dvorak
*Assistant Examiner* — Lindsay Regan Lancaster
(74) *Attorney, Agent, or Firm* — Patterson Thuente, P.A.

(57) ABSTRACT

A pulmonary treatment catheter and handle system including a catheter assembly with insertion tube coupled to a handle assembly. The system is further removably coupleable to a delivery device, such as a flexible bronchoscope or endoscope, having a port for coupling the handle assembly thereto, and a working channel in communication with the port for delivering the catheter assembly through the delivery device and into a body lumen. Optionally, a port channel of the port can be collinear with the working channel of the delivery device. The catheter assembly, handle assembly, and delivery device cooperate together to facilitate delivery and positioning of a catheter electrode in a treatment site, such as an airway, conduit, or vessel for treatment of the (Continued)

tissue, while minimizing damage to portions of the catheter assembly, the delivery device, or both.

17 Claims, 16 Drawing Sheets

(52) U.S. Cl.
CPC ...... *A61B 18/14* (2013.01); *A61B 2018/0022* (2013.01); *A61B 2018/00023* (2013.01); *A61B 2018/00541* (2013.01); *A61B 2018/00577* (2013.01); *A61B 2018/00982* (2013.01)

(58) Field of Classification Search
CPC .... A61B 2018/0022; A61B 2018/0054; A61B 2018/00982; A61B 1/018; A61B 2018/00172; A61B 2018/00577
See application file for complete search history.

(56) References Cited

U.S. PATENT DOCUMENTS

| | | | |
|---|---|---|---|
| 8,088,127 B2 | 1/2012 | Mayse et al. | |
| 8,489,192 B1 | 7/2013 | Hlavka et al. | |
| 9,138,343 B2* | 9/2015 | Stout | A61F 6/225 |
| 2006/0293560 A1* | 12/2006 | Nguyen | A61F 6/06 |
| | | | 600/104 |
| 2007/0005122 A1* | 1/2007 | Inoue | A61F 2/94 |
| | | | 623/1.11 |
| 2007/0288001 A1 | 12/2007 | Patel | |
| 2010/0191231 A1 | 7/2010 | Heberer | |
| 2010/0228084 A1* | 9/2010 | Sato | A61B 1/00133 |
| | | | 600/106 |
| 2010/0262140 A1 | 10/2010 | Watson et al. | |
| 2011/0152855 A1 | 6/2011 | Mayse et al. | |
| 2013/0289556 A1 | 10/2013 | Mayse et al. | |
| 2013/0324987 A1 | 12/2013 | Leung et al. | |
| 2014/0276764 A1* | 9/2014 | Shuman | A61B 18/1492 |
| | | | 606/41 |
| 2014/0336636 A1 | 11/2014 | Huszar et al. | |
| 2015/0366584 A1* | 12/2015 | Stout | A61B 17/42 |
| | | | 606/119 |
| 2016/0081745 A1* | 3/2016 | Rajagopalan | A61B 18/1492 |
| | | | 606/41 |
| 2016/0256307 A1* | 9/2016 | Longo | A61M 25/104 |

FOREIGN PATENT DOCUMENTS

| | | |
|---|---|---|
| JP | 2016511076 A | 4/2016 |
| WO | WO-2013028998 A2 | 2/2013 |
| WO | WO-2014159011 A1 | 10/2014 |
| WO | WO 2015/089377 A1 | 6/2015 |
| WO | WO-2015079322 A2 | 6/2015 |

OTHER PUBLICATIONS

PCT Written Opinion of the ISA for PCT/US2017/036773, dated Sep. 12, 2017, 6 pages.
International Search Report and Written Opinion for Application No. PCT/US2017/036773, dated Sep. 12, 2017, 9 pages.
Office Action dated Dec. 29, 2020 for Chinese Application No. 201780035621.5, 7 pages.

* cited by examiner

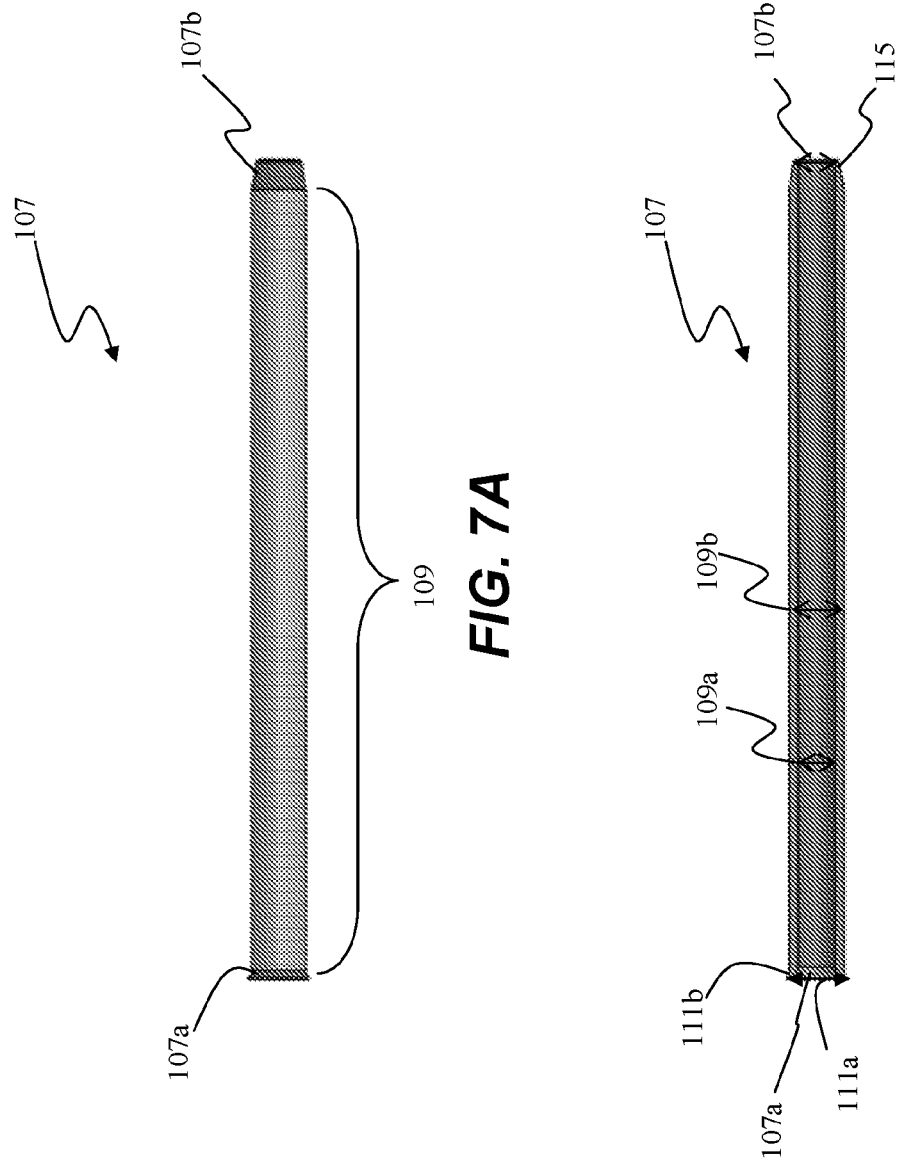

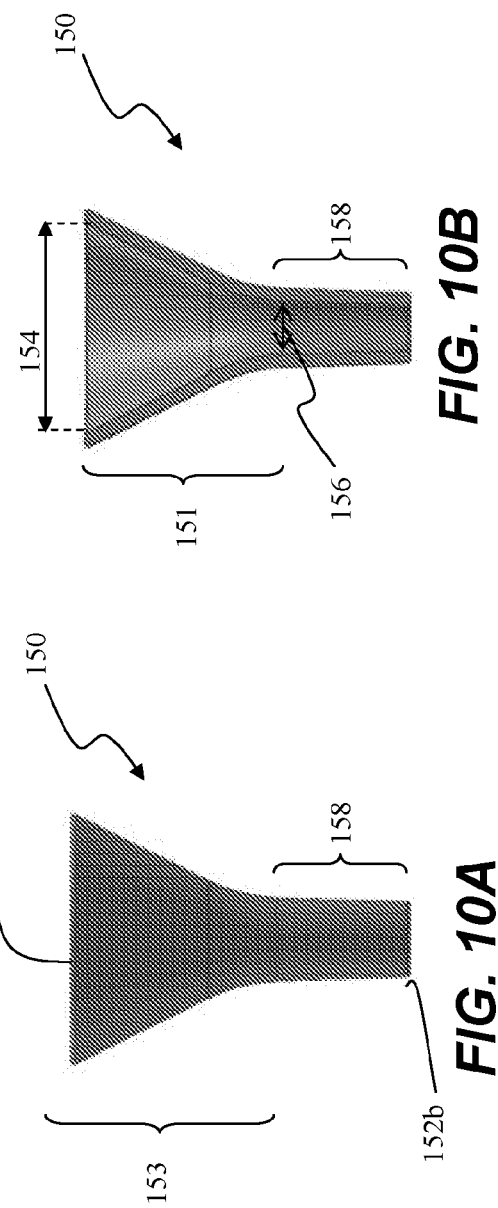

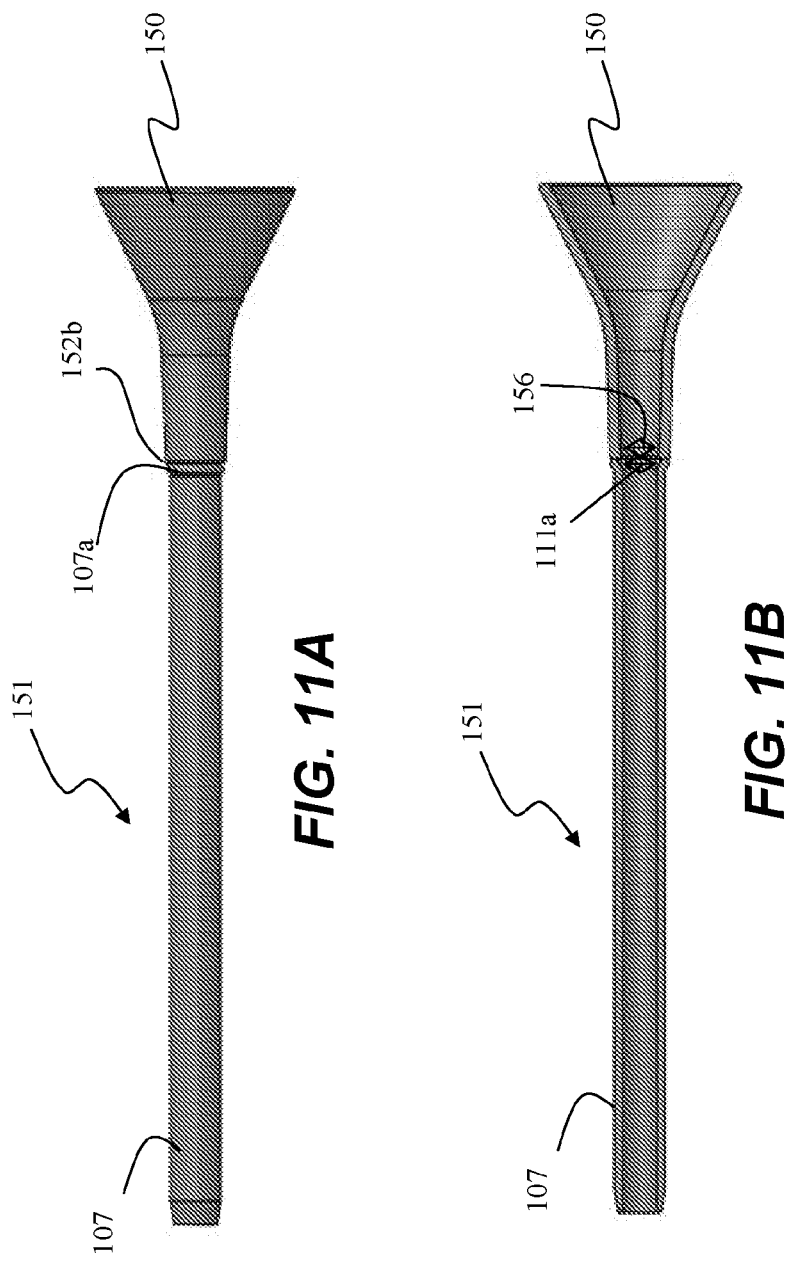

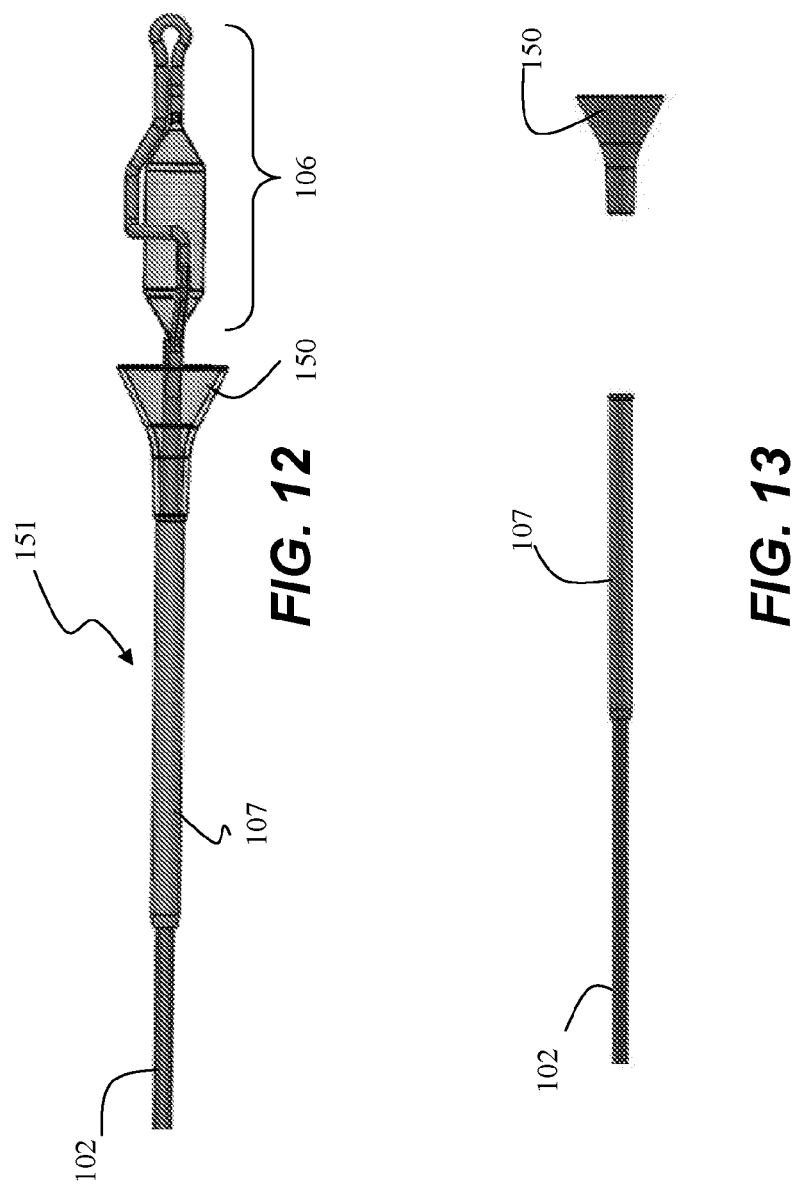

SYSTEMS AND METHODS FOR IMPROVED DELIVERY OF EXPANDABLE CATHETER ASSEMBLIES INTO BODY LUMENS

RELATED APPLICATION

The present application is a National Phase entry of PCT Application No. PCT/US2017/036773 which claims the benefit of U.S. Provisional Application No. 62/347,980 filed Jun. 9, 2016, which is hereby incorporated herein in its entirety by reference.

TECHNICAL FIELD

The invention relates generally to expandable catheter assemblies, and more particularly, to means for aiding delivery of an expandable catheter assembly via a delivery device into a body lumen for treatment.

BACKGROUND

Pulmonary diseases are some of the most common medical conditions, affecting tens of millions of people in the U.S. alone. Pulmonary diseases result from problems in the respiratory tract that interfere with proper respiration. Many of these diseases require medical attention or intervention in order to restore proper lung function and improve a patient's overall quality of life. Some of the more common pulmonary diseases include asthma and chronic obstructive pulmonary disease or COPD. Symptoms of pulmonary disease like COPD and asthma vary but often include a persistent cough, shortness of breath, wheezing, chest tightness, and breathlessness. Generally, these symptoms are exacerbated when performing somewhat strenuous activities, such as running, jogging, brisk walking, etc. However, these symptoms may be noticed when performing non-strenuous activities, if the disease is allowed to progress unchecked. Over time, especially if medical attention is not sought, a person's daily activities will be significantly impaired, thus reducing overall quality of life.

Many pulmonary diseases, whether acute or chronic, often involve pathologic conditions associated with airway inflammation. When such inflammation has developed at the airway, infiltrated inflammatory cells cause damage to bronchial or lung tissue, which eventually results in the respiratory dysfunction characteristic of pulmonary diseases, such as reduction in respiratory flow rate or oxygen exchange capacity. Over time, this inflammation can lead to blockage of the airway lumen, thickening of the airway wall, and alteration of structures within or around the airway wall. Airway obstruction can significantly decrease the amount of gas exchanged in the lungs resulting in breathlessness. Blockage of an airway lumen can be caused by excessive intraluminal mucus, edema fluid, or both. Thickening of the airway wall may be attributable to excessive contraction of the airway smooth muscle, airway smooth muscle hypertrophy, mucous glands hypertrophy, inflammation, edema, or combinations of these. Alteration of structures around the airway, such as destruction of the lung tissue itself, can lead to a loss of circumferential traction on the airway wall and subsequent narrowing of the airway. Generally, pulmonary diseases like COPD and asthma are the result of a complex interplay of local inflammatory cytokines, inhaled irritants (e.g., cold air, smoke, allergens, or other chemicals), systemic hormones (e.g., cortisol and epinephrine), local nervous system input (i.e., nerve cells contained completely within the airway wall that can produce local reflex stimulation of smooth muscle cells and mucous glands), and the central nervous system input (i.e., nervous system signals from the brain to smooth muscle cells and mucous glands carried through the vagus nerve).

Asthma can further include acute episodes or attacks of additional airway narrowing via contraction of hyper-responsive airway smooth muscle that significantly increases airflow resistance. Asthma symptoms include recurrent episodes of breathlessness (e.g., shortness of breath or dyspnea), wheezing, chest tightness, and coughing. Additionally, COPD, often referred to as emphysema, is characterized by the alteration of lung tissue surrounding or adjacent to the airways in the lungs. Emphysema can involve destruction of lung tissue (e.g., alveolar sacs) that leads to reduced gas exchange and reduced circumferential traction applied to the airway wall by the surrounding lung tissue. The destruction of alveoli tissue restricts the in-flow of oxygen rich air and the proper function of healthier tissue, resulting in significant breathlessness. Exposure to chemicals or other substances (e.g., tobacco smoke) may significantly accelerate the rate of tissue damage or destruction. Additionally, chronic bronchitis, another type of COPD, is characterized by contraction of the airway smooth muscle, smooth muscle hypertrophy, excessive mucus production, mucous gland hypertrophy, and inflammation of airway walls. Like asthma, these abnormalities are the result of a complex interplay of local inflammatory cytokines, inhaled irritants, systemic hormones, local nervous system, and the central nervous system. Unlike asthma where respiratory obstruction may be largely reversible, the airway obstruction in chronic bronchitis is primarily chronic and permanent.

Treatment for pulmonary diseases includes reducing exposure to harmful agents, administering medications (e.g., bronchodilators, steroids, phosphodiesterase inhibitors, theophylline, antibiotics, etc.), administering lung therapy (e.g., oxygen therapy, pulmonary rehabilitation), and surgical intervention, such as bronchial thermoplasty. Unfortunately, pharmacological treatment requires patient compliance, often causes harmful side effects, and does not necessarily treat the underlying cause of the disease. Similarly, surgical intervention can result in the destruction of smooth muscle tone and nerve function, such that the patient is unable to respond favorably to inhaled irritants, systemic hormones, and both local and central nervous system input.

An alternative method for treating pulmonary disease is referred to as targeted lung denervation. This method utilizes ablation, such as RF ablation, via an ablation assembly to selectively treat target regions inside of the airway wall (e.g., anatomical features in the stromas) while protecting the superficial tissues, such as the surface of the airway wall. For example, the mucous glands can be damaged to reduce mucus production a sufficient amount to prevent the accumulation of mucus that causes increased air flow resistance while preserving enough mucus production to maintain effective mucociliary transport, if needed or desired. Nerve branches/fibers passing through the airway wall or other anatomical features in the airway wall can also be destroyed.

Specially designed catheters allow for the introduction of an ablation assembly, generally comprising one or more collapsible electrodes or energy emitters, coupled to an expandable member, such as a balloon, into the airway of a patient via a delivery device. The delivery device can be a guide tube, a delivery sheath, a bronchoscope, or an endoscope and can include one or more viewing devices, such as optical viewing devices (e.g., cameras), optical trains (e.g., a set of lens), optical fibers, CCD chips, and the like. Once positioned in the desired region of the airway, such as the left and/or right main bronchi, the expandable member is expanded to position the one or more electrodes in contact with the airway wall.

Energy, such as RF energy, is supplied to the energy emitter to ablate the targeted tissue, causing a lesion to form, therefore temporarily or permanently damaging the targeted tissue, therefore affecting, e.g. attenuating nerve signals to or from, portions of the lungs associated with the targeted tissue. Simultaneously, a coolant is supplied through the catheter and is directed to the one or more electrodes and into the expandable member or balloon. This allows for cooling of the superficial tissue in contact with the electrode, as well as the adjacent tissues. The size, shape, and depth of the lesions are determined by the flow rate and temperature of the coolant, and the energy supplied to the energy emitter(s). Devices, systems, and methods of such procedures can be found, for example, in one or more of U.S. Pat. No. 8,088,127 entitled "Systems, Assemblies, and Methods for Treating a Bronchial Tree," and U.S. Patent Application Publication No. 2011/0152855 entitled "Delivery Devices with Coolable Energy Emitting Assemblies," both of which are incorporated herein by reference in their entireties.

In order to ensure that most or all of the target nerves extending along the airway are treated, it is generally desirable to form a circumferential lesion around all or most of the circumference of the airway wall. Due to design constraints or preferences, the electrode or energy emitter may not extend around the entirety of the circumference of the airway wall. Therefore, a circumferential lesion may be formed by ablating tissue while slowly rotating the ablation assembly or by positioning the ablation assembly in a series of rotational positions at each of which energy is delivered for a desired time period. The adjacent lesions then become contiguous and form a circumferential band all the way around the airway wall. Additionally or alternatively, the catheter may be repositioned axially to treat other locations within the airway distally or proximally of the first treatment site.

Typically targeted lung denervation is performed under bronchoscopic manipulation and visualization. A bronchoscope may be introduced into the target airway and the treatment catheter then delivered either alongside the bronchoscope or, more preferably, through the working channel of the bronchoscope. However, placement through the working channel can create challenges in manipulating the catheter due to the small size of the working channel, friction between the catheter and the walls of the working channel, and, in the case of flexible bronchoscopes, the curvature or tortuosity of the working channel. For example, as depicted in FIG. 1, the working channel of common commercially available flexible endoscopes or bronchoscopes 10 are accessed via a side port 11 (or "Y" pipe) located near the scope's handle 12, resulting in an angle between the side port 11 and the working channel of the handle 12 and flexible shaft 13 of the endoscope 10. Insertion of devices, such as needle probes, can result in damage to the working channel if the needle is not fully retracted, for example. In devices such as catheter and handle assemblies 14 comprising one or more collapsible electrodes or energy emitters 15 coupled to an expandable member 16, such as a balloon, advancing and/or retracting the device through this angulation can cause increased resistance or drag felt by the operator, which can in turn, hamper the operator's tactile feedback, and in certain scenarios, cause damage to the expandable member, energy emitters, or both.

To address these and other challenges, there remains a need for a system, device, or apparatus for delivery and manipulation of pulmonary treatment catheters, such as targeted lung denervation catheters, while minimizing the occurrence of damage to the catheter when positioning the catheter in a pulmonary airway through a delivery device such as the working channel of bronchoscope.

SUMMARY

Embodiments of the invention are directed to a pulmonary treatment catheter and handle system including a catheter assembly with insertion tube coupled to a handle assembly. The system is further removably coupleable to a delivery device, such as a bronchoscope or endoscope, having a port for coupling the handle assembly thereto, and a working channel in communication with the port for delivering the catheter assembly through the delivery device and into a body lumen. In embodiments, the catheter assembly, handle assembly, and delivery device cooperate together to facilitate delivery and positioning of a catheter electrode in a treatment site, such as an airway, conduit, or vessel for treatment of the tissue, while minimizing damage to portions of the catheter assembly, the delivery device, or both.

In certain embodiments, the catheter assembly comprises a targeted lung denervation (TLD) device, such as an RF, microwave, or ultrasound catheter, and generally includes an elongate shaft having proximal and distal portions, and an ablation assembly coupled to the distal portion of the shaft, the ablation assembly including an expandable member, such as a balloon or basket, and one or more electrodes or energy emitters coupled to the expandable member. The catheter assembly is further fluidly and electrically coupled to a system console, including a coolant supply and return reservoir, and an energy supply such as a RF generator, via the handle assembly.

In embodiments, the handle assembly is coupled to the proximal portion of the shaft of the catheter assembly. The handle assembly can include a housing fixedly coupled to the proximal end of the shaft, and a spindle tube or handle frame coupled to the housing such that the spindle tube is rotatably and axially shiftable with respect to the housing and the catheter assembly.

In embodiments, the handle assembly and catheter assembly are removably coupled to a delivery device, such as a flexible bronchoscope, in a single or unique orientation, or multiple orientations as desired by a user. In some aspects, the delivery device is a flexible bronchoscope including a rigid body or scope handle and a flexible shaft of a working length terminating at a distal working end. At least a portion of the flexible shaft is positioned within the body lumen to be treated. A working channel extends through the bronchoscope, in which a proximal end of the working channel terminates at a port formed on the rigid body, and a distal end of the working channel terminates at the working end of the flexible shaft. The elongate shaft and ablation assembly of the catheter can be inserted into the port via a port channel formed therethrough, and through the entirety of the working channel for delivery into the lumen via the working end of the flexible shaft.

In embodiments, the port is formed in the rigid body at a location such that the port channel is collinear with the working channel of the scope handle. This collinear port orientation allows for direct loading of the catheter assembly through the scope handle without the need to angle the catheter assembly as with the prior art side ports, which in turn reduces the resistance or drag on the catheter assembly and minimizes damage to the catheter assembly. In yet another embodiment, the port is pivotable with respect to the scope handle such that it can be shifted from a first insertion position in which the port channel is collinear with the working channel of the scope handle, and a second operating position in which the port channel is moved or tilted off axis or angled once the catheter assembly is inserted through the working channel and the handle assembly is coupled to the port. This allows for the handle assembly to be positioned relative to the scope body in a plurality of positions.

In embodiments, the catheter assembly includes an insertion tube moveably coupled to the shaft. In these embodiments, the insertion tube is longitudinally, and optionally rotationally, coupled to an outer surface of the shaft of the catheter assembly. The insertion tube is sized to guide the expandable ablation assembly positioned on the distal end of the shaft into the insertion tube when the ablation assembly is in a retracted configuration, e.g. an expandable balloon is deflated, and within the port channel of the delivery device, thereby providing a rigid support structure for introduction of the ablation assembly within the port channel. As the catheter assembly is being inserted through the working channel of the delivery device, the insertion tube translates or slides along the shaft of the catheter assembly from the ablation assembly toward the handle assembly. The insertion tube is also sized to nest within the handle assembly once the handle assembly is coupled to the port of the delivery device.

The systems and devices according to embodiments allows for easier insertion of the catheter assembly with expandable ablation assembly into and through a delivery device such as a flexible endoscope or bronchoscope than previous systems. The improved systems reduce the resistance or drag felt by the operator during use and reduce the occurrence of damage to the ablation assembly.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIG. 7A is a side elevational view of the insertion tube of FIG. 4

FIG. 7B is a cutaway view of the insertion tube of FIG. 7A.

FIG. 10A is a side elevational view of an insertion tube funnel according to an embodiment of the invention;

FIG. 10B is a cutaway view of the insertion tube funnel of FIG. 10A;

FIG. 11A is a side elevational view of the insertion tube funnel of FIG. 10A mated to the insertion tube of FIG. 7A, according to an embodiment of the invention;

FIG. 11B is a cutaway view of the insertion tube and insertion tube funnel assembly of FIG. 11A;

FIG. 12 is a side elevational view of the catheter and insertion tube assembly with insertion tube funnel mated thereto;

FIG. 13 is a side elevational view of the cathetheter and insertion tube assembly of FIG. 12 with insertion tube funnel detached therefrom;

Figure 1:
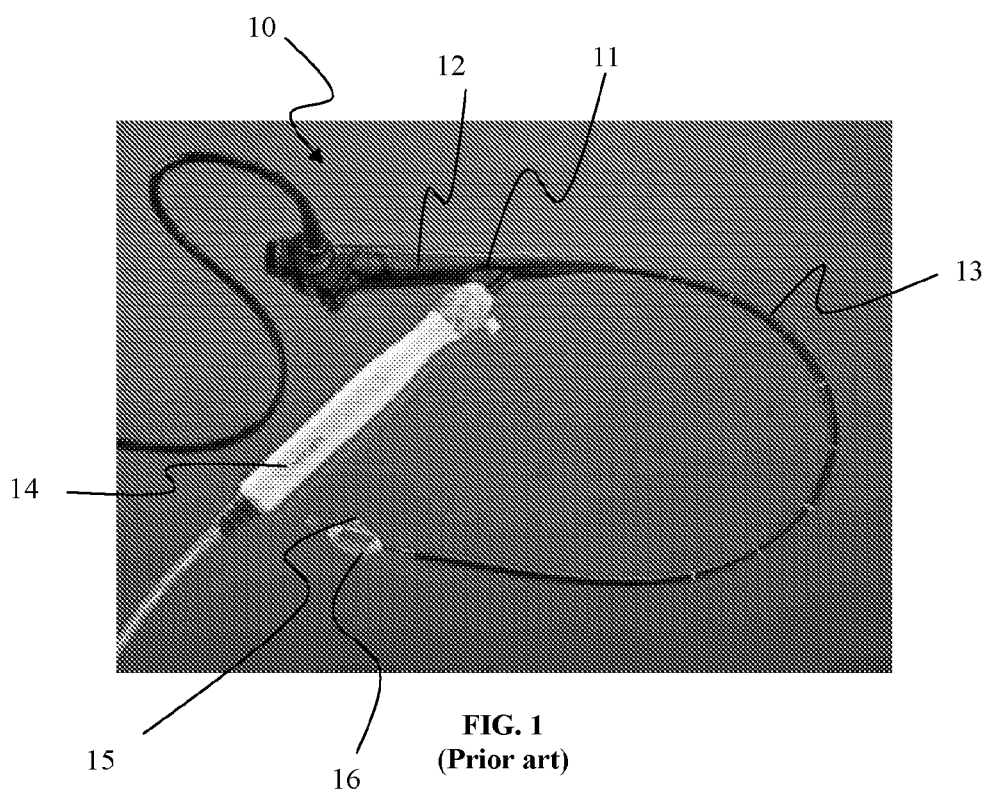
FIG. 1 is perspective view of a catheter and handle system coupled to an angled side port of a bronchoscope of the prior art.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Figure 2:
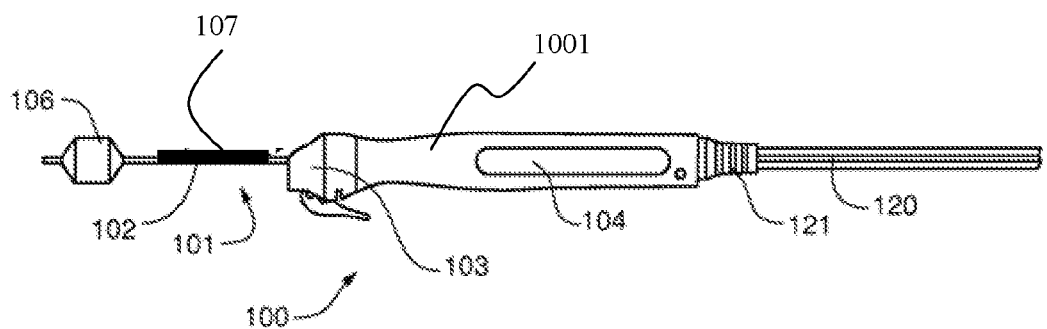
FIG. 2 is a side elevational view of a catheter and handle system according to an embodiment of the invention (insertion tube not shown)

According to some embodiments, as illustrated in FIG. 2, a catheter and handle system 100 for can comprise an ablation catheter assembly 101 having an elongate shaft 102 and an ablation assembly 106 coupled to a first or distal end of shaft 102, a positioning handle assembly 104 coupled to a second or proximal end of shaft 102, an insertion tube 107 movably coupled to shaft 102 between ablation assembly 106 and handle assembly 104, and a scope coupling assembly 103 for coupling catheter assembly 101 and handle assembly 104 to a working channel of a delivery device, such as a flexible endoscope or bronchoscope. Insertion tube 107 translates along shaft 102 from a first position in which ablation assembly 106 is retracted and compacted within insertion tube 107 at the distal end of shaft 102, and a second position in which insertion tube 107 is nested within handle assembly 104 when coupled to a port of the working channel of a delivery device (not shown).

Figure 3:
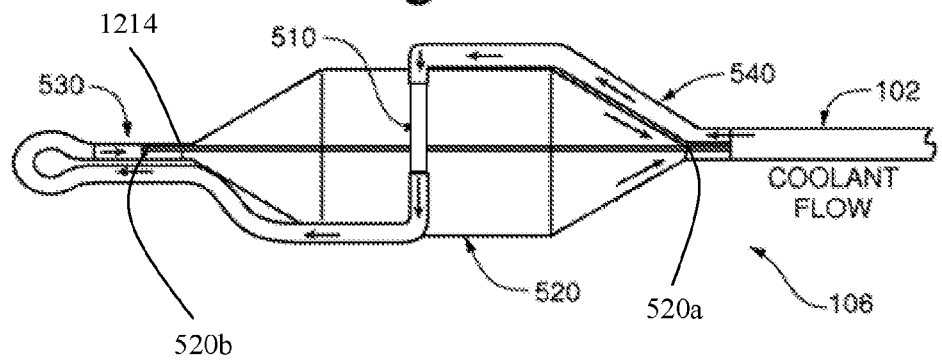
FIG. 3 is a side elevational view of an ablation assembly of a catheter assembly according to an embodiment of the invention.
Figure 5:
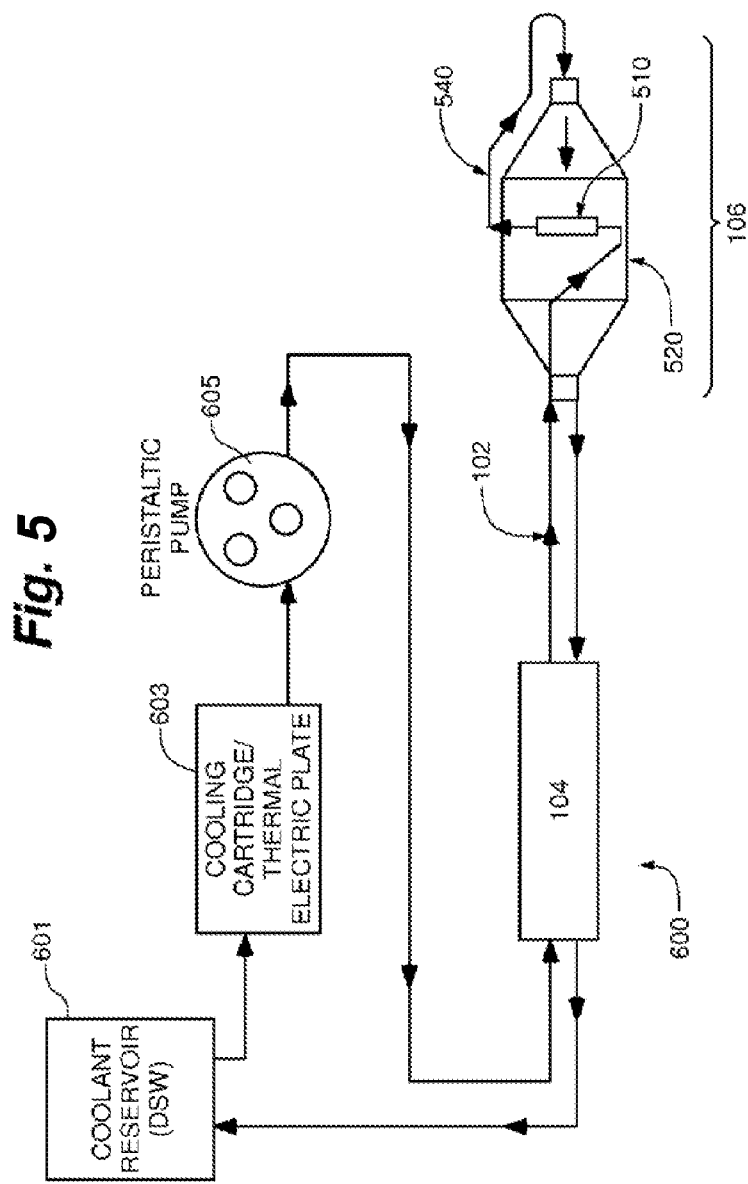
FIG. 5 is a flow diagram of a catheter and handle system according to an embodiment of the invention.
Figure 6:
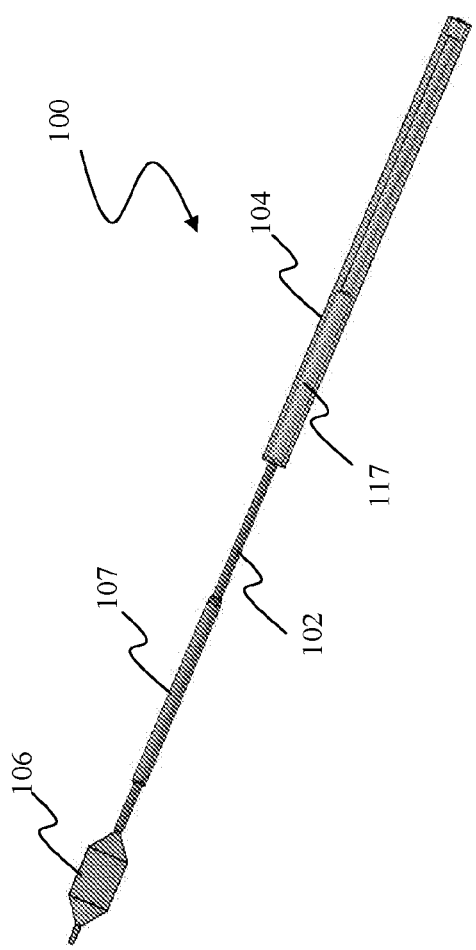
FIG. 6 is a perspective view of a catheter and handle assembly with insertion tube according to an embodiment of the invention.

Now referring to FIG. 3, ablation assembly 106 can comprise one or more energy emitters 510, such as an electrode or transducer, and an expandable member 520, such as a balloon or basket. One or more energy emitters are configured to delivery energy in the form of RF, microwave, or ultrasound, for example. In embodiments, one or more energy emitters is coupled to a conduit 540 configured for flowing coolant therethrough to cool energy emitters 510. Conduit 540 is in fluid communication with shaft 102 and expandable member 520 for circulating coolant. Referring to FIG. 5, ablation assembly 106 can comprise a coolant fluid path or cooling circuit 600 to cool energy emitter 510 and a surface of expandable member 520 to protect surface tissue in contact with energy emitter 510 and adjacent to energy emitter 510 to accomplish deep tissue ablation.

Referring back to FIG. 3, ablation assembly 106 can optionally comprise a throttle valve 530 for regulating the flow between conduit 540 and expandable member 520. Ablation assembly 106 can also optionally comprise a support wire 1214, such as a Nitinol wire, which extends along at least a length of catheter shaft 102 and between an interior of a proximal end 520a and distal end 520b of expandable member 520 to provide added axial, torsional, and buckling support for expandable member 520 and catheter shaft 102. Further details of ablation assemblies 106 are described in U.S. Pat. No. 8,088,127 entitled "Systems, Assemblies, and Methods for Treating a Bronchial Tree," and U.S. Patent Application Publication No. 2011/0152855 entitled "Delivery Devices with Coolable Energy Emitting Assemblies," both of which were incorporated by reference in their entireties above.

Figure 4:
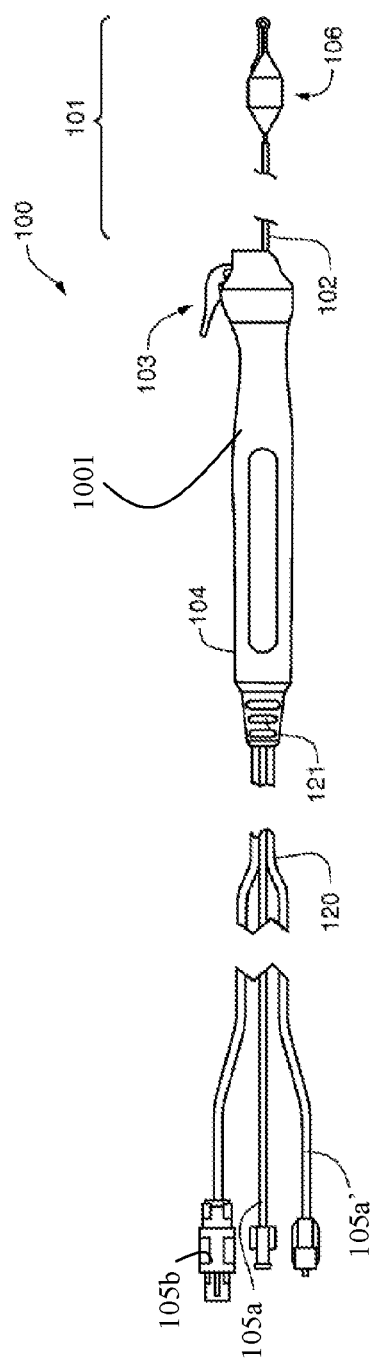
FIG. 4 is a side elevational view of a catheter and handle system of FIG. 2.

In some embodiments, and referring to FIGS. 2 and 4, handle assembly 104 is coupled to the proximal portion of shaft 102 of catheter assembly 101. Handle assembly 104 can include a housing 1001 fixedly coupled to the proximal end of shaft 102, and a spindle tube or handle frame (not shown) coupled to and within housing 1001 such that the spindle tube is rotatably and axially shiftable within housing 1001 and catheter assembly 101.

An umbilical cable 120 coupled to an end of handle assembly 104 via strain relief 121 for fluidly and/or electrically coupling catheter assembly 101 to accompanying devices or accessories, such as a power source, energy source (e.g. RF generator), fluid or coolant supply, heat exchanger, and controller, preferably combined in a system console. Umbilical cable 120 can include, for example, connections for inlet and return fluid tubes or lumens 105a, 105a' for fluidly coupling shaft 102 to a fluid or coolant supply, from the console which optionally includes a heat exchanger for cooling and/or heating input fluid, and one or more electrical cable/connector 105b to electrically connect the shaft and/or ablation assembly to a power source, thermocouples for temperature monitoring, and/or pressure sensors for coolant circuit pressures. In other embodiments, handle assembly 104 can comprise an internal battery source for operating handle assembly 104 and any accompanying devices or accessories. Suitable handle assemblies are described in more detail in International Publication No. WO 2015/089377 A1, entitled "Catheter and Handle Assembly, Systems, and Methods", incorporated herein by reference in its entirety.

Catheter assembly 101 is further fluidly and electrically coupled to a system console (not shown), including a coolant circuit (at 600 shown in FIG. 5) including coolant supply and return reservoir, and an energy supply such as a RF generator, via handle assembly 104. Handle assembly 104 is configured to maneuver the distal portion or end of shaft 102 and therefore ablation assembly 106 in axial and circumferential directions during the administration of treatment, such as targeted lung denervation (TLD) therapy, details of which are discussed in U.S. Pat. No. 8,088,127 and U.S. Patent Application Publication No. 2011/0152855, both of which were incorporated by reference in their entireties above.

As depicted in FIG. 5, cooling circuit 600 includes coolant supplied from a reservoir 601 of a system console, through an optional heat exchanger 603 of the system console, through handle 104, through an inflow lumen in shaft 102, through conduit 540 to which electrode 510 is coupled, through expandable member 520, through an outflow lumen in shaft 102, through handle 104, and back to the system console. Non-limiting examples of a system console can be found in U.S. Patent Application Publication No. 2013/0289556, entitled "Delivery Devices with Coolable Energy Emitting Assemblies" and U.S. Pat. No. 8,489,192 entitled "System and Method for Bronchial Dilation," both of which are incorporated by reference in their entireties. Cycling of the fluid is accomplished, for example, by a peristaltic pump 605. In an alternative embodiment, the flow is reversed such that the coolant flows through the expandable member before the electrode.

Catheter assembly 101 and handle assembly 104 are configured to be removably coupled to a delivery device, such as, for example, a guide tube, a delivery sheath, a bronchoscope, or an endoscope, via an insertion port (shown at 11 in FIG. 1 and at 113 in FIG. 9, for example). The delivery device can include one or more viewing devices, such as optical viewing devices (e.g., cameras), optical trains (e.g., a set of lens), and the like. In one particular embodiment, the delivery device comprises a flexible bronchoscope. Ablation assembly (not shown) and elongate shaft 102 are inserted into a working channel port of the device. Handle assembly 104 is then secured to the device via a scope coupling assembly 103. Scope coupling assembly 103 can be integral with or coupled to handle assembly 104, or can be its own stand-alone adapter coupling to both handle assembly 104 and the port. Scope coupling assembly 103 securely fits to the port, such as by frictional or abutting fit, locking lever, threaded engagement of corresponding threads, bayonet or snap fit, spring loaded fit, or any of a variety of mechanisms known to those skilled in the art. Once secured, scope coupling assembly 103 is fixed axially and rotationally with respect to the delivery device. More details regarding the coupling assembly 103 are also described in International Publication No. WO 2015/089377 A1, previously incorporated by reference in its entirety.

Now referring specifically to FIGS. 6-8B, insertion tube 107 is longitudinally, and optionally rotationally, movably and coaxially coupled to shaft 102 between ablation assembly 106 and handle assembly 104. Referring to FIGS. 7A and 7B, tube 107 has a constant inner diameter 109a and outer diameter 109b along an elongate portion 109 extending between first or distal end 107a and second or proximal end 107b. In an alternative embodiment, elongate portion 109 has varying diameters along its length. For example, elongate portion 109 can be ovalized such that the diameter is largest in the center of elongate portion 109 and decreases towards each end. Alternatively, elongate portion 109 is reduced or tapered from the ends inward towards the center such that the smallest diameter is in the center.

In an embodiment, first end 107a is flared, i.e. inner diameter 111a and outer diameter 111b angles radially outwardly from inner and outer diameters 109a, 109b, respectively, to create a taper that guides ablation assembly 106 into an inside diameter 111a of insertion tube 107. In an embodiment, outer diameter 111b of insertion tube 107 at flared end 107a is dimensioned to mate, i.e. create a friction fit, within a working channel of an insertion port 113 of a delivery device (not shown in FIGS. 7A and 7B).

Inner diameter 109a is dimensioned so that ablation assembly 106 can fold and compact within tube 107, allowing ablation assembly 106 to be delivered safely and easily into the working channel of the delivery device.

Second end 107b of insertion tube 107 defines a tapered outside diameter 115 that is less than outer diameter 109b. This taper allows insertion tube 107 to be guided into an internal recess or pocket 117 of handle assembly 104 (shown at 117 in FIG. 6) such that insertion tube 107 can completely or substantially nest within the housing of handle assembly 104.

Insertion tube 107 can be made from any of a variety of suitable rigid or semi-rigid materials, such as, but not limited to, polyethylene, polypropylene, PTFE polymer, or blends thereof. In one particular embodiment, insertion tube 107 is formed of a polymeric material, such as PTFE, having a low coefficient of friction allowing tube 107 to slide easily along shaft 102 and allowing ablation assembly 106 to slide within tube 107.

Figure 8A:
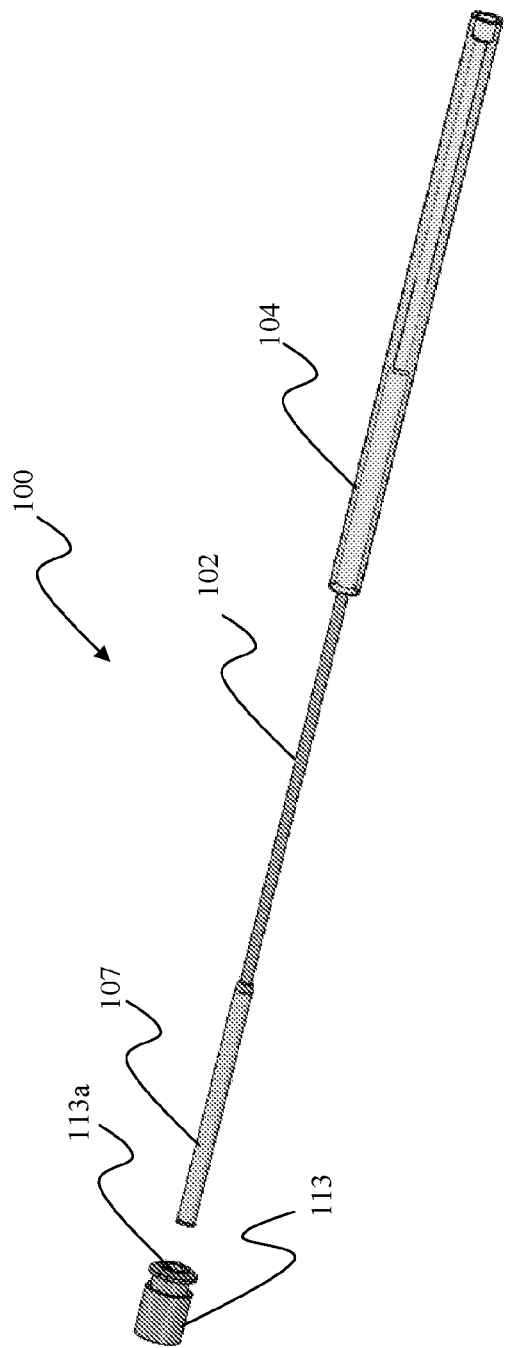
FIG. 8A is a perspective view of the catheter and handle assembly with insertion tube in a first insertion position.
Figure 8B:
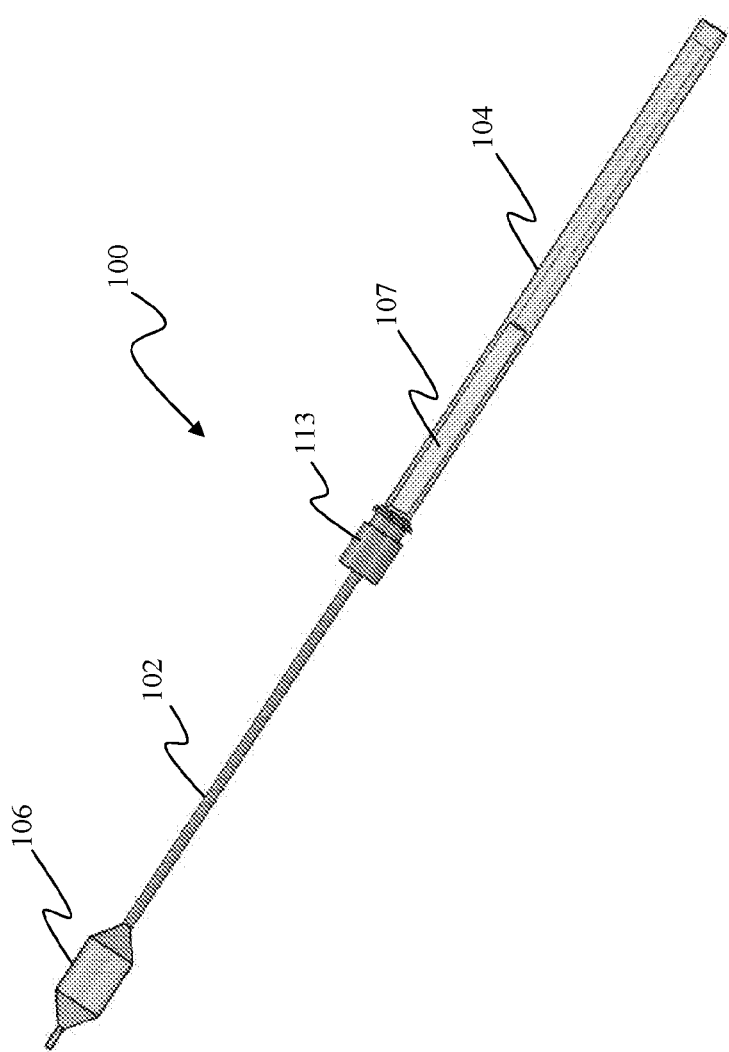
FIG. 8B is a perspective view of the catheter and handle assembly with insertion tube in a second nested position.

Referring now to FIGS. 8A-B, in use, insertion tube 107 translates along shaft 102 from a first position in which ablation assembly 106 is retracted and compacted within insertion tube 107 at the distal end of shaft 102 (FIG. 8A), and a second position in which insertion tube 107 is nested within handle assembly 104 when coupled to a port 113 of a delivery device (FIG. 8B). More specifically, as shown in FIG. 8A, tube 107 is slid over ablation assembly 106 such that tube 107 completely or substantially covers compacted or deflated ablation assembly 106. Tube 107 is then inserted into an insertion port 113 formed on a delivery device (not shown).

Catheter assembly 101 is advanced through working channel 113a of the delivery device (not shown) by moving handle assembly 104 towards port 113. As handle assembly 104 moves towards port 113, tube 107 stays fixed to port 113 and shaft 102 moves through tube 107 until handle assembly 104 slides over tube 107 and contacts port 113, allowing ablation assembly 106 to be deployed, as depicted in FIG. 8B. Tube 107 nests completely or substantially within handle assembly 104 such that handle assembly 104 can be secured to port 113, as described in more detail below.

Figure 9A:
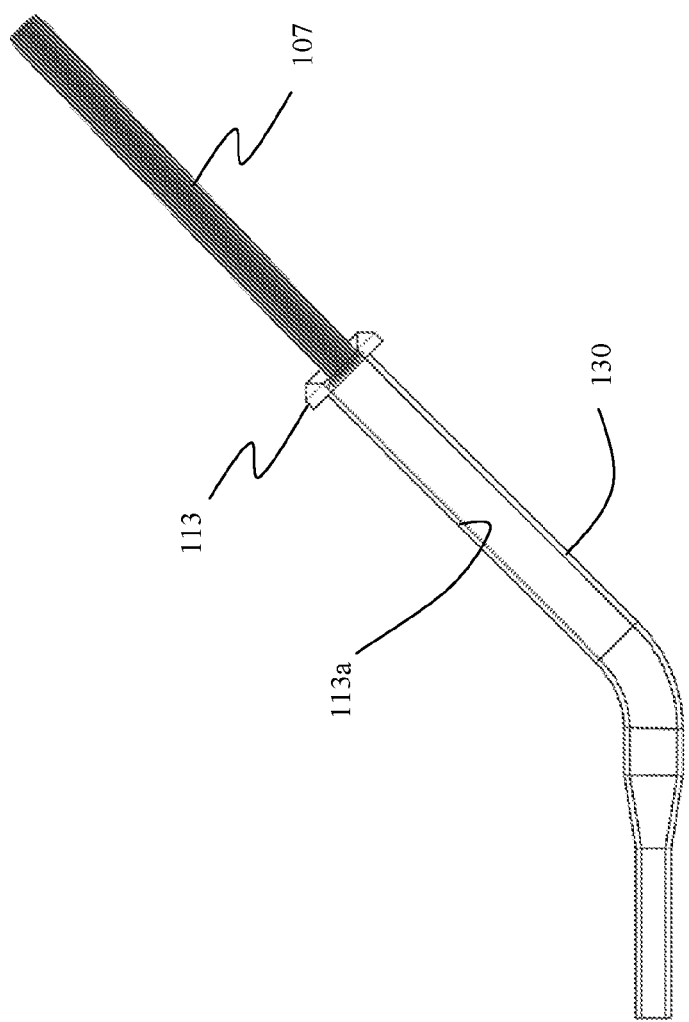
FIG. 9A is a side cross-sectioned elevational view of an insertion tube and a delivery device according to an embodiment of the invention.
Figure 9B:
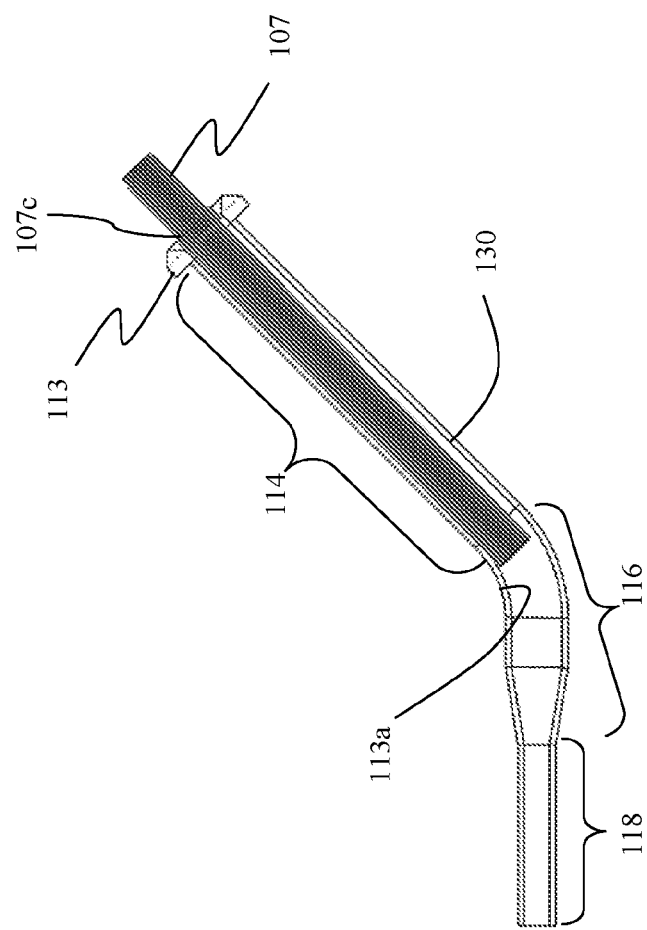
FIG. 9B is a side cross-sectioned elevational view of an insertion tube and a delivery device according to another embodiment of the invention.
Figure 9C:
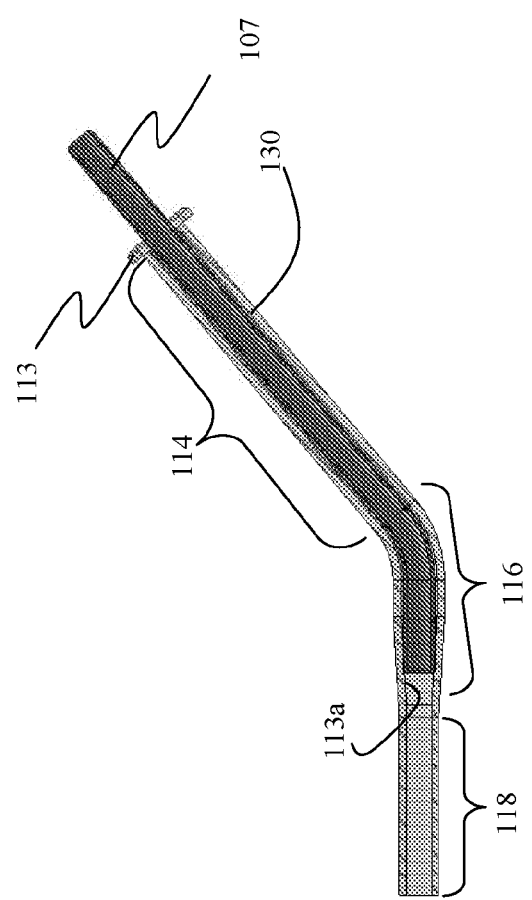
FIG. 9C is a side cross-sectioned elevational view of an insertion tube and a delivery device according to yet another emobdimetn of the invention.

Referring now to FIGS. 9A-9C, insertion tube 107 may be inserted partially or substantially into a delivery device 130. As depicted in FIG. 9A, insertion tube 107 is placed into insertion port 113 without substantially entering working channel 113a. In this embodiment, the flared first end 107a prevents insertion tube 107 from extending beyond port 113 such that insertion tube 107 does not extending within the working channel 113a for any appreciable length.

In an alternative arrangement depicted in FIG. 9B, insertion tube 107 is configured to be inserted substantially into a linear portion 114 of working channel 113a of delivery device 130. In this embodiment, first end 107a is not flared so that insertion tube 107 can pass through port 113 and working channel 113a. First end 107a can be a same diameter of the insertion tube 107, or may be tapered, similar to second end 107b.

As described above, insertion tube 107 can be constructed from a material having a low coefficient of friction, allowing ablation assembly 106 to easily slide within tube 107. However, various delivery devices 130 may not necessarily include a smooth, low-friction working channel 113a, and the arrangement of FIG. 9B reduces the distance that ablation assembly 106 travels through working channel 113a of delivery device 130, decreasing the potential for damage to ablation assembly 106. In this embodiment, tube 107 has a length that is greater than linear portion 114 of working channel 113a such that a portion of tube 107 remains exterior to working channel 113a and port 113, and will nest within handle 104 when handle 104 is coupled to port 113. In this embodiment, insertion tube 107 can optionally include a flange 107c configured to interfere with port 113 so as to limit insertion of tube 107 into working channel 113a. Flange 107c can be formed on tube 107 along a length that is substantially similar to a length of linear portion 114 of working channel 113a. In this embodiment, ablation assembly 106 moves along linear portion 114 of working channel 113a within insertion tube 107, and exits tube 107 in a non-linear portion 116 of working channel 113a, and into a flexible portion 118 of working channel 113a.

In yet another alternative arrangement depicted in FIG. 9C, insertion tube 107 is configured to be inserted substantially into a linear portion 114 of working channel 113a and through at least a portion of non-linear portion 116 of delivery device 130. In this embodiment, first end 107a is not flared so that insertion tube 107 can pass through port 113 and working channel 113a. First end 107a can be a same diameter of the insertion tube 107, or may be tapered, similar to second end 107b, to accommodate a tapered junction between non-linear portion 116 and flexible portion 118.

As described above, insertion tube 107 can be constructed from a material having a low coefficient of friction, allowing ablation assembly 106 to easily slide within tube 107. The material is rigid enough to allow ablation assembly 106 to past through, yet pliable so that insertion tube 107 flexes to navigate the curve of non-linear portion 116. The arrangement of FIG. 9C reduces the distance that ablation assembly 106 travels directly through working channel 113a of delivery device 130, decreasing the potential for damage to ablation assembly 106, such as by snagging around the curve of non-linear portion 116.

In this embodiment, tube 107 has a length that is greater than a total length of linear portion 114 and non-linear portion 116 of working channel 113a such that a portion of tube 107 remains exterior to delivery device 130, and will nest within handle 104 when handle 104 is coupled to port 113. In this embodiment, insertion tube 107 can optionally include a flange (not shown) configured to interfere with port 113 so as to limit insertion of tube 107 into working channel 113a. Such flange can be formed on tube 107 along a length that is substantially similar to a length of linear portion 114 and at least a portion of a length of non-linear portion 116 of working channel 113a. In this embodiment, ablation assembly 106 moves along linear portion 114 and at least some of non-linear portion 116 of working channel 113a within insertion tube 107, and exits tube 107 at an end a non-linear portion 116 of working channel 113a that is collinear to flexible portion 118 of working channel 113a.

In some embodiments, and now referring to FIGS. 10A-13, an insertion tube funnel 150 can be mated to end 107a (e.g. flared end 107a) of insertion tube 107 as a tube and funnel assembly 151 to help collapse and slide ablation assembly 106 into insertion tube 107. Funnel 150 is configured to extend a contact point of ablation assembly 106 away from the axis, placing less stress on components of ablation assembly 106, such as a 90 degree elbow of conduit 540 while aiding the folding of conduit 540 within funnel 150.

Referring now to FIGS. 10A and 10B, insertion tube funnel 150 extends between a first end 152a and a second end 152b, and can comprise a frustoconical section 153 with a major inner diameter 154 at first end 152a, which tapers along a length of funnel 150 to a minor inner diameter 156. An elongate stem section 158 extends from minor inner diameter 156 of frustoconical section 153 to second end 152b of funnel 150. In embodiments, a diameter of stem section 158 is constant along its length and is substantially equal to minor inner diameter 156. In alternative embodiments, stem section 150 has a varying diameter along its length.

Referring to FIGS. 11A and 11B, second end 152b of funnel 150 is appropriately sized to engage end 107a such as by friction fit, by threaded coupling, snap fit, or any other coupling mechanisms. Preferably, minor inner diameter 156 is sized to mate with inner diameter 111a of end 107a of insertion tube 107, creating a smooth lead in transition from funnel 150 to insertion tube 107.

In use, and referring to FIG. 12, funnel 150 is mated to insertion tube 107 such that catheter shaft 102 extends through funnel 150 and insertion tube 107, thereby aligning ablation assembly 106 axially with funnel 150. As insertion tube 107 with funnel 150 coupled thereto are slid along shaft 102 and pulled over ablation assembly 106, major diameter 154 of funnel 150 captures ablation assembly 106 and compacts and folds ablation assembly 106 to decrease a profile of assembly 106, allowing it to fit completely within insertion tube 107, as shown in FIG. 13. Once ablation assembly 106 is loaded into insertion tube 107, funnel 150 is no longer needed, and is removed from insertion tube 107, allowing insertion tube to be mated with a port of a delivery device, as discussed above.

In some embodiments, funnel 150 is disposable and configured for one time use, and can comprise, for example, a polymer material having a low coefficient of friction, such as polyethylene. In other embodiments, funnel 150 can comprise coated or uncoated paper, foil, rubber material, plastic, such as, for example, polyethylene, polypropylene, polytetrafluoroethylene (PTFE), or similar, or any of a variety of materials having a low coefficient of friction. In alternative embodiments, funnel 150 is reusable, and is formed of a material that is durable enough to be sterilized between uses, such as by autoclaving.

Figure 14:
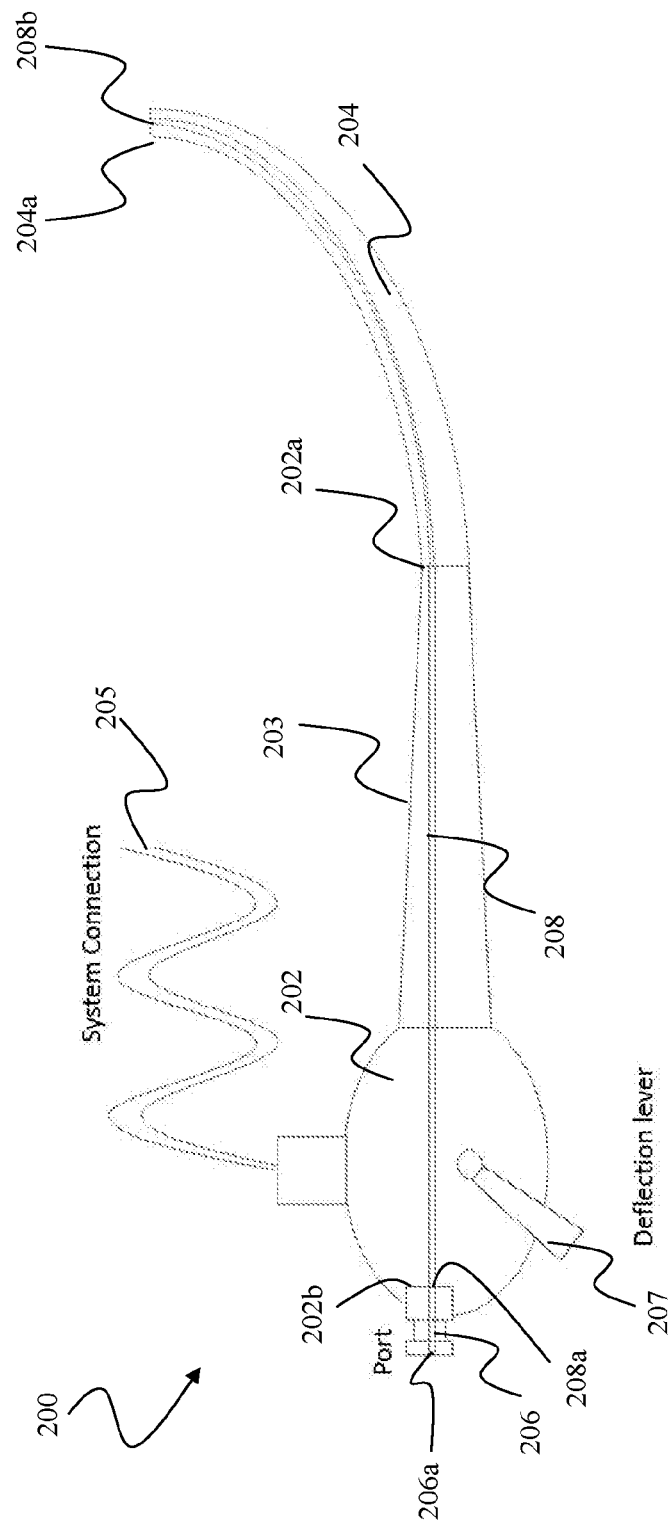
FIG. 14 is a side view of a delivery device having a collinear port and working channel according to an embodiment of the invention.

In some embodiments, and referring to FIG. 14, a delivery device 200 for improved delivery of the catheter and handle system into a lumen to be treated can comprise a flexible endoscope or bronchoscope including a rigid scope body 202 and rigid elongated section 203, a flexible shaft 204 coupled to a first, distal end 202a of elongated section 203, a working channel 208 defined therethrough, and a straight or collinear port 206 formed in a second, proximal end 202b of body 202. Delivery device 200 can comprise various optional components, such as, for example, system connections 205 (e.g. electrical, optical cables or fiber optics), deflection levers 207, fiber optics, suction, and the like. These various components can be positioned to the side of port 206 and working channel 208. In one particular example, a CCD chip is incorporated into the working end of shaft 204, thereby eliminating the need for fiber optics running parallel to or along working channel 208.

In embodiments, working channel 208 is collinear with a port channel 206a at proximal end 202b, extends through body 202, and along shaft 204, ending at 208b at a working end 204a of shaft 204. The catheter assembly (not shown) is introduced into port 206, and through channel 208 until the ablation assembly is delivered through working channel end 208b into a lumen to be treated. Aligning working channel 208 with port channel 206a such that no angle is created between allows for direct loading of the catheter assembly through the scope body without the need to angle the catheter assembly as with the prior art side ports, which in turn reduces the resistance or drag on the catheter assembly and minimizes damage to the catheter assembly.

Figure 15:
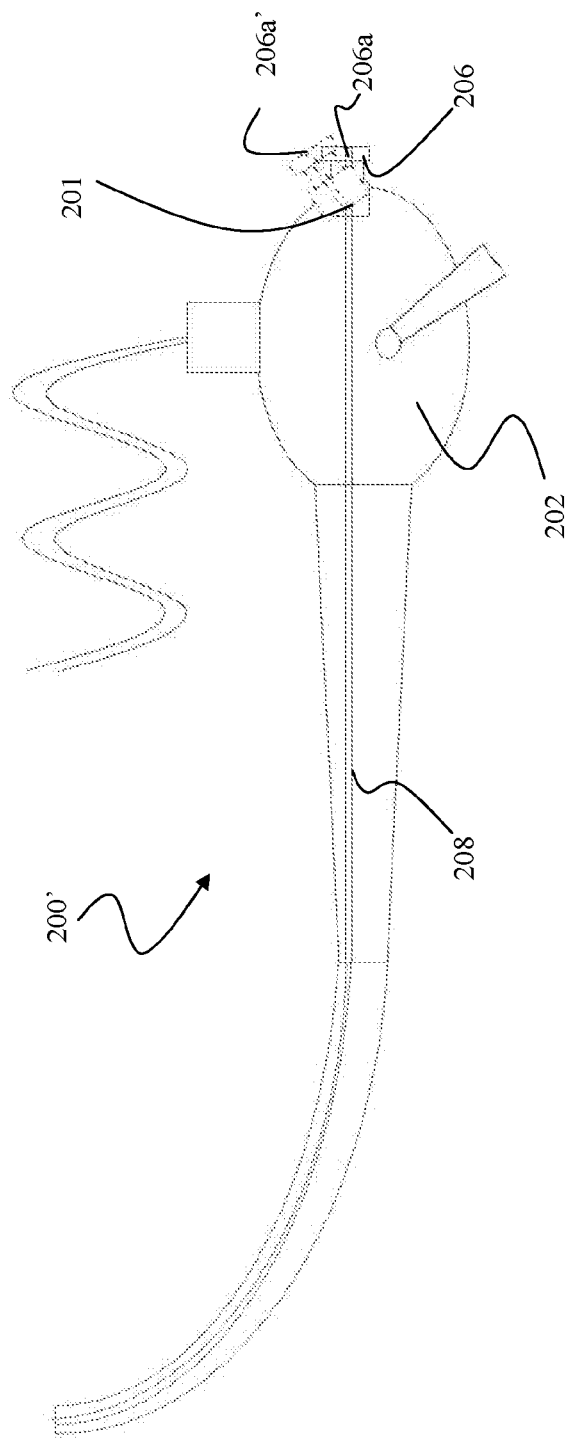
FIG. 15 is a side view of a delivery device having a pivotal port according to an embodiment of the invention.

In another embodiment, as referring to FIG. 15, port 206 of device 200' is pivotably mounted via a pivot pin 201 to body 202 such that port 206 can be shifted from a first position in which port channel 206a is collinear with working channel 208 of body 202, and a second angled position (shown in phantom) in which port channel 206a' is tilted off axis or angled with respect to working channel 208. In use, for example, a catheter assembly can be introduced into port 206 when in the first position for ease of loading the ablation assembly into working channel 208. Once the catheter assembly is inserted through the working channel and the handle assembly is coupled to port 206, port 206 is pivoted from the first collinear position. This allows for the catheter and handle assembly to be positioned relative to the scope body in a plurality of positions, as desired by the operator. Port 206 can then be moved back to the first position as desired, such as, for removal or repositioning of the catheter assembly.

Delivery device 200 can be used in combination with or as an alternative to catheter and handle system 100 with insertion tube 107, to improve delivery of the ablation assembly through the working channel and into the body lumen to be treated.

The systems and devices according to embodiments allows for easier insertion of the catheter assembly with expandable ablation assembly into and through a delivery device such as a flexible endoscope or bronchoscope than previous systems. The improved systems operate to reduce the resistance or drag felt by the operator during use and reduce the occurrence of damage to the ablation assembly during loading, use, and unloading.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A system for ablating target tissue of an airway of a patient, the system comprising:
   a catheter assembly including—
      an elongate shaft having a proximal end and a distal end;
      a positioning handle assembly coupled to the proximal end of the elongate shaft;
      an ablation assembly coupled to the distal end of the elongate shaft, the ablation assembly being configured to be positioned within the airway to deliver energy to the target tissue, the ablation assembly including—
         an expandable member movable between a retracted configuration and an expanded configuration, and
         an energy emitter coupled to the expandable member, wherein energy emitter is configured to be positioned proximate the target tissue when the expandable member is in the expanded position; and
      an insertion tube having a substantially smooth outer surface and slidably positioned over the elongate shaft, the insertion tube being configured and dimensioned to move between a first position in which the ablation assembly, in the retracted configuration, is compacted within the insertion tube, and a second position in which the ablation assembly extends outside of the insertion tube and the insertion tube is nested entirely within the handle assembly; and
   a controller configured to deliver energy from an energy source to the energy emitter.

2. The system of claim 1, wherein the insertion tube comprises:
   an elongate portion having a constant inner diameter and outer diameter; and
   a first flared end in which the inner diameter and outer diameter angles outwardly from the constant inner and outer diameter, wherein the first flared end is dimensioned to urge the retracted ablation assembly within the insertion tube.

3. The system of claim 2, wherein the flared end terminates in a flange.

4. The system of claim 2, wherein the insertion tube further comprises:
   a second tapered end opposite the first flared end, wherein an outer diameter of the second tapered end is less than the constant outer diameter, thereby forming a chamfer.

5. The system of claim 1, wherein the catheter assembly further comprises a funnel removably couplable to a first end of the insertion tube, the funnel being configured to fold the ablation assembly into a compacted configuration when the expandable member is in the retracted configuration for insertion into the insertion tube.

6. The system of claim 1,
   wherein the handle assembly includes a housing forming an internal recess, wherein the insertion tube is configured to nest partially or entirely within the housing when the insertion tube is in the second position.

7. The system of claim 6, wherein the system is coupleable to a port of a delivery device for delivering the ablation assembly into the airway, wherein:
   the insertion tube is configured to be coupled to the port when the insertion tube is in the first position; and
   the insertion tube is configured to shift to the second position as the handle assembly moves toward and into contact with the port causing the ablation assembly to move through a working channel of the delivery device and into the airway, in which at least a portion of the insertion tube is nested within the handle assembly.

8. The system of claim 1, wherein the system is coupleable to a port of a delivery device for delivering the ablation assembly into the airway, further wherein:
   the insertion tube is configured to be inserted through the port and at least partially into a working channel of the delivery device.

9. The system of claim 8, wherein the working channel of the delivery device includes a linear portion and a non-linear portion, wherein a first end of the linear portion is coupled to the port, and a second end of the linear portion is coupled to the non-linear portion, further wherein:
   the insertion tube extends within and at least partially along the linear portion of the working channel.

10. The system of claim 9, further wherein the insertion tube extends through the linear portion and at least partially along and within the non-linear portion.

11. The system of claim 8, wherein the insertion tube includes a flange configured to limit the distance the insertion tube is inserted into the working channel.

12. A method for delivering an ablation assembly into an airway of a patient, the method comprising:
   providing a catheter assembly including—
      an elongate shaft having a proximal end and a distal end;
      a positioning handle assembly coupled to the proximal end of the elongate shaft;
      an ablation assembly coupled to the distal end of the elongate shaft, the ablation assembly being configured to be positioned within the airway to deliver energy to the target tissue, the ablation assembly including—
         an expandable member movable between a retracted configuration and an expanded configuration, and
         an energy emitter coupled to the expandable member, wherein energy emitter is configured to be positioned proximate the target tissue when the expandable member is in the expanded position; and
      an insertion tube having a substantially smooth outer surface and slidably positioned over the elongate shaft and movable between the proximal end and the distal end;
   sliding the insertion tube over the ablation assembly when the expandable member is in the retracted configuration;
   coupling the insertion tube with the ablation assembly therein to an insertion port of a delivery device; and
   moving the ablation assembly and elongate shaft through a working channel of the delivery device while the insertion tube is fixed to the insertion port, wherein the insertion tube is entirely nested with in the handle assembly.

13. The method of claim 12, further comprising:
providing a handle assembly coupled to the proximal end of the elongate shaft the handle assembly including a housing dimensioned to nest the insertion tube within, wherein moving the ablation assembly and elongate shaft through a working channel of the delivery device while the insertion tube is fixed to the insertion port comprises moving the handle assembly towards and into contact with the insertion port such that the insertion tube is partially or entirely nested within the housing.

14. The method of claim 13, further comprising:
fixedly coupling the handle assembly to the port.

15. The method of claim 12, further comprising, before sliding the insertion tube over the ablation assembly:
coupling a funnel to a first end of the insertion tube proximate the ablation assembly, the funnel being configured to fold the ablation assembly into a compacted configuration for insertion into the insertion tube.

16. The method claim 12, wherein coupling the insertion tube with the ablation assembly therein to an insertion port of a delivery device comprises:
inserting the insertion tube through the port and at least partially into the working channel of the delivery device.

17. The method of claim 16, wherein the working channel of the delivery device includes a linear portion and a non-linear portion, wherein a first end of the linear portion is coupled to the port, and a second end of the linear portion is coupled to the non-linear portion, wherein coupling the insertion tube with the ablation assembly therein to an insertion port of a delivery device comprises:
inserting the insertion tube through an entirety of the linear portion and at least partially into the non-linear portion.

* * * * *